United States Patent [19]

Sethofer

[11] 4,335,011
[45] Jun. 15, 1982

[54] CYCLOHEXYL-DIOXANE LIQUID CRYSTALLINE COMPOUNDS

[75] Inventor: Nicholas L. Sethofer, San Jose, Calif.

[73] Assignee: Timex Corporation, Waterbury, Conn.

[21] Appl. No.: 268,464

[22] Filed: May 29, 1981

Related U.S. Application Data

[62] Division of Ser. No. 135,381, Mar. 28, 1980, Pat. No. 4,298,528.

[51] Int. Cl.$^3$ ............................ C09K 3/34; G02F 1/13; C07D 319/04
[52] U.S. Cl. ................................ 252/299.1; 252/299.5; 252/299.61; 549/369; 549/372; 549/374
[58] Field of Search ............ 252/299.61, 299.5, 299.1; 260/340.7

[56] References Cited

U.S. PATENT DOCUMENTS

| 3,947,375 | 3/1976 | Gray et al. | 252/299.66 |
|---|---|---|---|
| 3,997,536 | 12/1976 | Doller et al. | 252/299.61 |
| 4,118,335 | 10/1978 | Krause et al. | 252/299.66 |
| 4,130,502 | 12/1978 | Eidenschimk et al. | 252/299.63 |
| 4,180,475 | 12/1979 | Schadt et al. | 252/299.61 |
| 4,198,130 | 4/1980 | Doller et al. | 252/299.5 |
| 4,200,580 | 4/1980 | Hsu | 252/299.61 |
| 4,298,528 | 11/1981 | Sethofer | 252/299.61 |
| 4,313,878 | 2/1982 | Hsu | 252/299.61 |

FOREIGN PATENT DOCUMENTS

| 139852 | 1/1980 | German Democratic Rep. | 252/299.61 |
|---|---|---|---|
| 139867 | 1/1980 | German Democratic Rep. | 252/299.61 |
| 2257588 | 6/1977 | Fed. Rep. of Germany | 252/299.61 |
| 2044767 | 10/1980 | United Kingdom | 252/299.1 |
| 2063288 | 6/1981 | United Kingdom | 252/299.1 |

OTHER PUBLICATIONS

Sorkim, H., Mol Cryst. Liq. Cayst., vol. 56 (Letters), pp. 279-281 (1980).
Gray, G. W., Mol. Cryst. Liq. Cryst., vol. 63, pp. 3-18 (1981).
Demus, D., et al., Mol. Cryst. Liq. Cryst., vol. 63, pp. 129-144 (1981).
Doller, A., et al., Mol. Cryst. Liq. Cryst., vol. 42, pp. 215-231 (1977).

Primary Examiner—Teddy S. Gron
Attorney, Agent, or Firm—William C. Crutcher; Edward J. Timmer

[57] ABSTRACT

Novel liquid crystalline compounds having low viscosity, low transition temperatures, positive dielectric anisotropy and extremely low optical birefringence are provided. The compounds are represented by the formula:

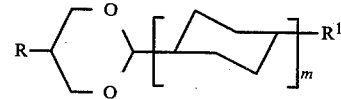

where R and $R^1$ can be the same or different straight chain alkyl or alkoxy group and m can be 1 or 2.

Guest-host electrooptical displays including a mixture of one or more of the compounds with a suitable pleochroic dye exhibit much improved contrast and low driving voltage while eliminating the need for polarizers and excessive dye additions.

7 Claims, No Drawings

CYCLOHEXYL-DIOXANE LIQUID CRYSTALLINE COMPOUNDS

This application is a division, of application Ser. No. 135,381, filed Mar. 28, 1980, now U.S. Pat. No. 4,298,528.

FIELD OF THE INVENTION

The present invention relates to electrooptical displays of the guest-host type and to liquid crystalline host materials for use in such displays.

DESCRIPTION OF THE PRIOR ART

The family of electrooptical display devices known generally as guest-host devices are thought to have high potential utility for information display purposes such as digital watches or clocks, calculators and other instruments. The typical guest-host device includes a pair of flat, parallel transparent substrates carrying transparent electrode segments on their facing surfaces and a mixture of nematic liquid crystal host compound and guest dichroic dye compound sealed between the substrates and electrodes. In this arrangement, the guest dye molecules tend to assume the orientation of the host liquid crystal molecules relative to the spaced substrates. The construction and operation of such guest-host electrooptical display devices are well known as shown in the Helmeier U.S. Pat. No. 3,551,026 issued Dec. 29, 1970.

In one type of guest-host display, the host liquid crystal molecules and therefore the guest dye molecules are aligned with their long axis parallel (homogenous) to the spaced substrates in the unactivated (off) state. However, when an electric field is generated across the electrode segment, the liquid crystal molecules align perpendicularly (homeotropically) to the substrates as do the guest dye molecules. Since the dichroic dye molecules absorb only light whose electric vector lies along the long dye axis, the homeotropically aligned dye molecules absorb little light and the liquid crystal-dye mixture between activated electrode segments appears essentially colorless or transparent to the viewer of incident light. Of course, homogenously aligned areas of the mixture appear colored or dark as a result of the perpendicular orientation of the dye molecules to the incident light. A display having light or colorless digites or symbols on a dark or color background is thereby provided.

However, guest-host display devices of this type suffer from a serious drawback in that, at best, the homogenously aligned dye molecules will absorb only 50% of the light incident upon the device, thereby resulting in poor display contrast. This limitation is due to the fact that only one polarization direction of the incident light has its electric vector aligned along the long axis of the dye molecule while the other polarization direction has its electric vector aligned transverse to the long dye axis. One attempted solution to this drawback has been to use well-known substrate surface alignment techniques such as rubbing or slope evaporation to induce a 90° twist (helix) in the long axis of the homogenously aligned liquid crystal molecules from one substrate to the other much as in the well known twisted nematic liquid crystal electrooptical display devices, for example, see the Taylor and White U.S. Pat. No. 3,833,287 issued Sept. 3, 1974 and Coates and Gray U.S. Pat. No. 4,145,114 issued Mar. 20, 1979. The purpose of this helical molecular structure is to ensure that no matter what the orientation of the electric vector of the incident light, there will be a dye molecule at some distance between the spaced substrates with its long axis parallel to the vector to effect absorption. Thus, absorption of 95% or more of the incident can be effected. Unfortunately, however, as is well known in conventional twisted nematic liquid crystal devices, the host liquid crystal exhibits a positive birefrigence and tends to act as an optical waveguide so that the polarization of light transmitted through the device is twisted synchronously with the twist of the long axes of the liquid crystal molecules that the light is passing through. The unfortunate net effect is that the twisted guest-host display made with positive birefringent liquid crystal compounds is optically equivalent to a non-twisted homogenously aligned guest host device with the attendant poor contrast.

The possibility of utilizing a host liquid crystal or mixtures thereof with minimal birefringent properties in such twisted guest-host display devices in order to increase contrast was initially proposed by Taylor in the *Journal of Applied Physics* 45(11), November 1974 at page 4,721. However, a practical mixture of liquid crystal compounds with low enough birefringence has not up to the present time been known or developed by prior art workers. The cyclohexyl cyclohexane compounds first synthesized by Eidenschink et al., *Angew. Chem.* 133, p. 90 (1978) apparently do not have low enough birefringent properties for twisted guest-host displays and mixtures containing these compounds are sometimes smectic rather than nematic at room temperature.

A copending patent application U.S. Ser. No. 17,635 filed Mar. 5, 1979, now abandoned, in the name of Howard Sorkin and of common assignee herewith discloses liquid crystal compounds of the formula:

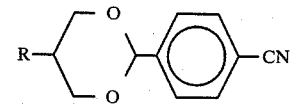

where R is alkyl, alkoxy, aryl, aryloxy, carboxy or carboxy ester. These compounds have a very low electrical threshold voltage of approximately 0.6 volt, and relatively low optical birefringence of $\Delta n$ equal to 0.1.

A copending patent application U.S. Ser. No. 17,634, now U.S. Pat. No. 4,200,580 filed Mar. 5, 1979 in the name of Yin Yen Hsu and of common assignee herewith discloses compounds of the formula:

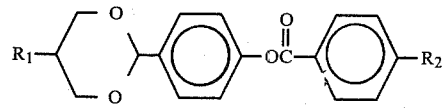

where $R_1$ is a straight chain alkyl of 1 to 10 carbon atoms and $R_2$ is alkyl, alkoxy, acyloxy, alkyl carbonato having 1 to 10 carbons, CN or $NO_2$.

What is still needed, however, is a nematic liquid crystalline material having extremely low optical birefringence along with the other required properties to provide a guest host display with improved contrast.

SUMMARY OF THE INVENTION

According to the present invention, there is provided a new group of compounds which for the first time exhibit the aforementioned required combination of properties, in particular extremely low optical birefringence and low threshold voltages.

The compounds of the invention are represented by the formulas:

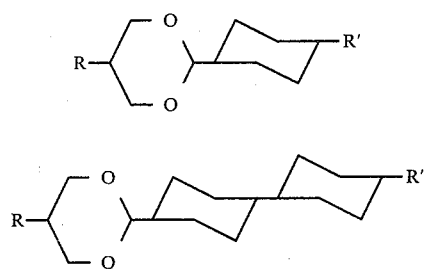

where R and $R^1$ can be the same or different straight chain alkyl or alkoxy groups. Alkyl substituents are preferred to provide compounds with extremely low optical birefringence, e.g. $\Delta n$ values of 0.05 or below, preferably 0.005 or below.

In addition, there is provided an improved guest host electrooptical display of excellent contrast and low driving voltage as a result of employing as the optical guest host medium the aforesaid compounds in admixture with a suitable well-known pleochroic dye such as dyes having an order parameter equal to or greater than 0.72.

DESCRIPTION OF PREFERRED EMBODIMENTS

The compounds of the present invention may be prepared as follows:

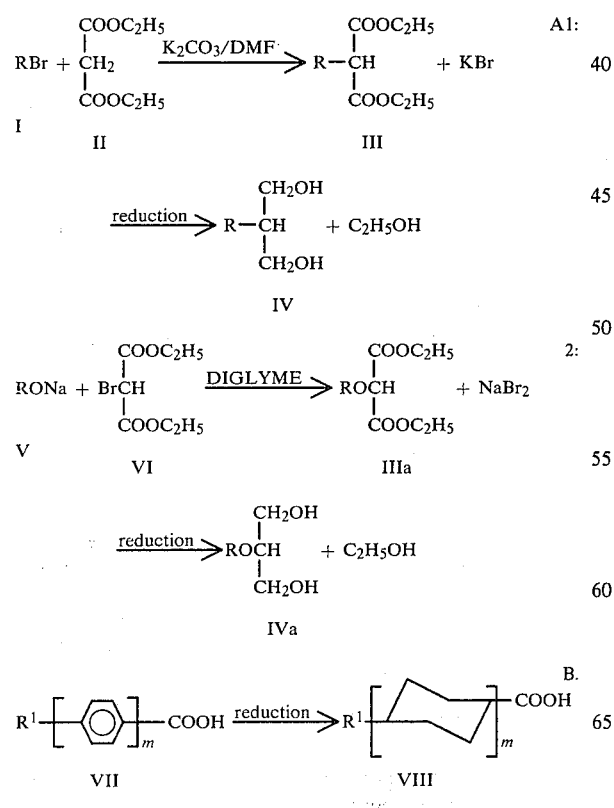

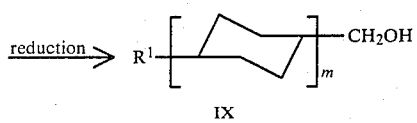

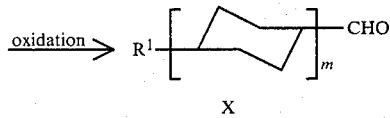

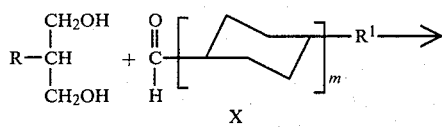

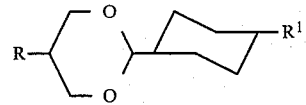

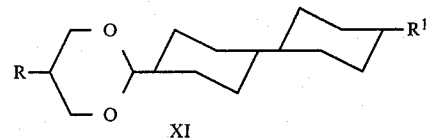

where R, $R^1$ and m are as described hereinabove.

The alkylation of malonic acid esters was carried out with potassium carbonate in dimethyl formamide for convenience with the reaction mixture being stirred for one week at room temperature to yield 90% and above of compound III.

The reduction of the R-substituted malonic acid esters was carried out by subsequent reactions with borane methyl sulfide complex followed by Vitride reducing agent (e.g. sodium-bis-(2-methoxy-ethoxy) aluminum hydride). Combination of these reactants provided yields over 80% of compound IV or IVa.

The p-alkyl or alkoxy benzoic acids (compound VII) used were either commercially available or prepared according to well known methods.

Compound VIII, 4-alkyl or alkoxy cyclohexyl carboxylic acid, was prepared by hydrogenation using either sodium metal in isoamyl alcohol (trans isomer separated from cis by crystallization in pentane) or, preferably, by catalytic hydrogenation over rhodium. The resulting predominantly cis isomer was transformed to trans with sodium methoxide in pyrrolidine, although other methods may be employed.

Reduction of the carboxyl groups of compound VIII to methanol to yield compound IX was carried out with Vitride reducing agent with yields over 95%. Oxidation of compound IX to alkyl or alkoxy cyclohexyl carboxaldehyde was then achieved with dimethyl sulfoxide and N,N'-dicyclohexylcarbodiimide and pyridiniumtrifluoro acetate as the catalyst. A mild, room temperature reaction had yields of 70% and above of compound X.

The dioxane compounds of the present invention are obtained as both trans and cis isomers, typically in a 3:1 ratio. The isomers can be readily separated by crystallization from hexanes, pentanes or other well known solvents. The trans configuration is the one which presumably accounts for the nematic characteristics of the subject compounds.

The following examples are offered for purposes of illustration, rather than limitation, and provide a more detailed description of the subject dioxane compounds.

EXAMPLE 1

5-Propyl-2-(4 Heptylcyclohexyl)-1,3 Dioxane (A) Formation of 2-propyl-1,3 propanediol (compound IV)

To a 3 liter, 3 neck round bottom flask fitted with a condenser for merely precautionary purposes and an air-driven stirrer the following materials are added:
(1) 150.53 ml (1 mole) of diethyl malonate
(2) 109 ml (1.2 mole) of n-propyl bromide
(3) 166 gm (1.2 mole) of potassium carbonate
(4) 400 ml of N,N-dimethylformamide The flask is fitted with a thermometer and the reaction mixture is stirred for seven days at room temperature. The temperature of the mixture rises to about 40° C. for about 2-3 hours and then drops to and stays at room temperature for the remainder of the time. Samples for gas chromatography are taken periodically and reveal the following:

| TIME (hrs) | N-PROPYL BIOMIDE | DIETHYL MALONATE | N-PROPYL DIETHYL MALONATE |
|---|---|---|---|
| 0 | 41.82% | 58.18% | 0 |
| 21 | 8.14% | 17.77% | 74.09% |
| 42.5 | 3.44% | 9.78% | 86.78% |
| 65 | 1.76% | 7.65% | 90.59% |
| 168 | 0.87% | 5.64% | 93.49% |

The propyl diethyl malonate is isolated by vacuum distillation and then reduced in a 3-neck round bottom flask in a mixture of the following:
(1) 1500 ml (3 mole) borane-methyl sulfide complex in toluene (2 M solution)
(2) 101 gm (0.5 mole) propyl diethyl malonate
(3) 300+300 ml toluene
(4) 650 ml (2.25 mole ) Vitride T The BMS complex is added to a mixture of propyl diethyl malonate and toluene dropwise with stirring at room temperature. This partial mixture is stirred for an additional one hour at room temperature after the BMS has been added and then is refluxed with stirring for ten hours, colled to 20° C., and transferred into an additional funnel and added carefully (dropwise) into a refluxing mixture of toluene and Vitride T. After this addition, refluxing continues for another 30 minutes and then the complete mixture of (1)-(4) is cooled to room temperature and transferred to a large beaker. A solution of $H_2SO_4/H_2O$ in 1:3 ratio is added to the complete mixture with stirring until the pH is 5 to 6. Then, the complete mixture is diluted with methanol and organic salts are removed by filtration and washed successively with methanol. At this stage, a single layer of filtrate is obtained, solvents are evaporated and gas chromatography reveals 82% of 2-propyl-1,3 propanediol in the raw product. Vacuum distillation at 80°-85° C. and 0.75-1.1 mmHg provided a 70% yield and 98.9% purity.

B. Formation of trans-4-heptyl-cyclohexyl carboxaldehyde (compound X)

Introduce 84 ml (0.3 mole) Vitride reducing agent and about 250 ml dry benzene into a 3-neck flask fitted with a condenser and bring to reflux. Within 30 minutes, add dropwise a solution of 30 gm (0.1 mole) trans-4-heptylcyclohexyl carboxylic acid in benzene and continue to reflux for additional 3-4 hours. Mixture is then cooled to 20°-30° C. and introduced slowly with stirring into a 20% HCl aqueous solution plus ice. After addition, the mixture is vigorously stirred for another 20 minutes. The resulting layers are then separated. The organic portion is washed with water and dried over $MgSO_4$ and the solvent is removed by evaporation. Purification of the intermediate, trans-4-heptyl-cyclohexyl methanol was not necessary as gas chromatography showed 99.9 purity and yield of 98.7%.

The next step involved mixing the following in a suitable flask with magnetic stirring bar:
(1) 19.11 gm (0.09 mole) trans-4-heptyl-cyclohexyl methanol
(2) about 100 ml benzene
(3) about 100 ml (excess) dimethyl sulfoxide
(4) 7.5 ml (0.09 mole) pyridine
(5) 3.6 ml (0.045 mole) trifluoroacetic acid
(6) 55.8 gm (0.27 mole) N,N'-dicyclohexyl carbodiimide with the trifluoroaceticacid being added last to the mixture. The flask was sealed with a drying tube and the mixture stirred at room temperature for 16 hours. The mixture is then transferred to a large beaker and oxalic acid is added in small portions (foaming occurs) to destroy any excess of $N,N^1$-dicyclohexyl carbodiimide. Then the mixture is filtered and the solid portion (dicyclohexyl urea) is washed several times with benzene. The organic filtrate is washed with a solution of sodium bicarbonate and several times with water. The solvent is then evaporated and the raw aldehyde treated with a concentrated sodium bisulfite solution. The solid complex obtained is thoroughly and repeatedly washed in ether, then treated in potassium carbonate solution in water. The trans-4-heptyl-cyclohexyl carboxaldehyde product is extracted with benzene and the solvent evaporated. The yield was 87% and purity by gas chromatography was 97.2%.

C. Formation of 5-propyl-2-(4-heptylcyclohexyl)-1,3-dioxane

To a 3-liter, 3-neck round bottom flask fitted with a condenser, Dean-Stark trap and air-driven stirrer, the following are introduced:
(1) 16.54 gm (0.14 mole) 2-propyl-1,3-propanediol
(2) 21.5 gm (0.102 mole) trans-4-heptyl-cyclohexyl-carboxaldehyde
(3) 450 ml benzene
(4) Trace p-toluene sulfonic acid.

The mixture is brought to reflux and the water removed azeotropically. Refluxing is continued for 6-8 hours (although it is observed that all calculated amount of water has formed within first 20 minutes). Then the benzene is removed by evaporation and the residue checked by gas chromatography. The raw compounds are found to contain two main portions with identical infra-red spectra (combined peaks being 95.6% and remainder being impurities). The ratio of trans/cis isomers was found to be 3.16/1.

Separation of the isomers and purification of the trans isomer of 5-propyl-2-(4-heptycyclohexyl)-1,3-dioxane was carried out by crystallization from pentane and hexane three times. Gas chromatography of the purified compound revealed 99.914% purity, the remaining 0.086% being most probably one of the higher homologues. No cis isomer was detected at this stage.

Transition temperatures for trans-5-propyl-2-(4-heptylcyclohexyl)-1,3-dioxane as measured on a Perkin-Elmer DSC-2 machine were as follows:

C-N (crystal-nematic) = 45.4° C.
N-I (nematic-isotropic) = 49.9° C.
Δn(optical birefringence) = 0.048

Other exemplary compounds have been prepared by the synthesis procedures set forth hereinabove and are listed below along with corresponding properties.

EXAMPLE 2

5-Ethyl-2-(4-Pentylcyclohexyl)-1,3-Dioxane

C-N = 19.9° C.
I-N = (17.5°) monotropic nematic

Δn = 0.004

EXAMPLE 3

5-Ethyl-2-(4-Heptylcyclohexyl)-1,3-Dioxane

C-I (crystal-isotropic) = 41.3° C.
I-S (isotropic-smectic) = (35.9° C.) monotropic smectic

EXAMPLE 4

5-Butyl-2-(4-Heptylcyclohexyl)-1,3-Dioxane

C-S (crystal-smectic) = 29.2° C.
S-I (smectic-isotropic) = 57.3° C.

EXAMPLE 5

5-(Ethyl-2-(4-(4'Pentylcyclohexyl) cyclohexyl)-1,3-Dioxane

C-N = 175.8° C.
N-I = 180.2° C.

In the examples, Δn values were determined by measurements in a wedge cell according to well known procedures.

The above examples illustrate that a variety of physical and nematic properties can be obtained by varying the length and shape of terminal substituents of 2-cyclohexyl substituted 1,3-dioxanes. To achieve extremely low Δn values (optical birefringence), it is preferred to employ alkyl terminal substituents. For greater thermal stability, it is preferred to employ alkoxy terminal substituents or two six membered saturated rings. Compounds of the invention having two six membered saturated rings exhibit higher optical birefringence than those with only one such ring and will be useful in raising clearing points of cyclohexyl-dioxane mixtures when included in small weight percentages.

While there has been described what is considered to be preferred embodiments of the invention, other embodiments or modifications will occur to those skilled in the art and it is desired to cover in the appended claims all such embodiments and modifications as fall within the true spirit and scope of the invention.

I claim:

1. In an electrooptical display including a liquid crystalline material, the improvement wherein the liquid crystalline material comprises a compound of the formula:

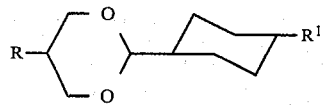

where R and $R^1$ can be the same or different straight chain alkyl or alkoxy group.

2. In a guest-host electrooptical display including a host liquid crystalline material admixed with a guest dye material, the improvement wherein the host liquid crystalline material comprises a compound of the formula:

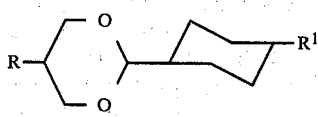

where R and $R^1$ can be the same or different straight chain alkyl or alkoxy group.

3. In a guest-host electrooptical display including a host liquid crystalline material admixed with a guest dye material, the improvement wherein the host liquid crystalline material comprises a compound of the formula:

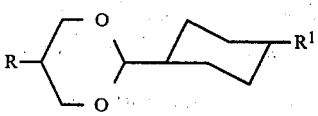

where R and $R^1$ are the same or different straight chain alkyl group.

4. The guest-host electrooptical display of claim 3 wherein the host liquid crystalline material includes a compound of the stated formula where R is propyl and $R^1$ is heptyl.

5. The guest-host electrooptical display of claim 3 wherein the host liquid crystalline material includes a compound of the stated formula where R is butyl and $R^1$ is heptyl.

6. The guest-host electrooptical display of claim 3 wherein the host liquid crystalline material includes a compound of the stated formula where R is ethyl and $R^1$ is heptyl.

7. In a guest-host electrooptical display including a host liquid crystalline material admixed with a guest dye material, the improvement wherein the host liquid crystalline material comprises a compound of the formula:

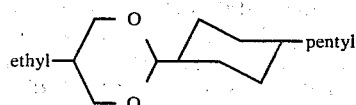

* * * * *